United States Patent [19]

Kihara

[11] Patent Number: 5,254,768
[45] Date of Patent: Oct. 19, 1993

[54] PROCESS FOR PRODUCING 3,3',4,4'-TETRAMETHYLDIPHENYLMETHANE

[75] Inventor: Shuta Kihara, Hiratsuka, Japan

[73] Assignee: Mitsubishi Gas Chemical Company, Inc., Tokyo, Japan

[21] Appl. No.: 832,712

[22] Filed: Feb. 7, 1992

[30] Foreign Application Priority Data

Mar. 1, 1991 [JP] Japan .................. 3-059444

[51] Int. Cl.$^5$ .................................. C07C 5/22
[52] U.S. Cl. ........................ 585/477; 585/481; 585/470; 585/475
[58] Field of Search ............ 585/477, 481, 470, 475

[56] References Cited

U.S. PATENT DOCUMENTS

| | | | |
|---|---|---|---|
| 3,636,177 | 1/1972 | Suzuki et al. | 585/477 |
| 4,173,573 | 11/1979 | Shulz et al. | 549/242 |
| 4,962,260 | 10/1990 | Sikkenga et al. | 585/481 |

OTHER PUBLICATIONS

Chemical Abstracts, vol. 86, No. 25, May 20, 1977, abstract no. 189435k of JP 76 38710, Yataro Ichikawa et al., "Isomerization of dimethylbiphenyls".

*Primary Examiner*—Asok Pal
*Assistant Examiner*—P. Achutamurthy
*Attorney, Agent, or Firm*—Frishauf, Holtz, Goodman & Woodward

[57] ABSTRACT

There is provided a process for producing 3,3',4,4'-tetramethyldiphenylmethane which comprises subjecting tetramethyldiphenylmethane containing at least one of 2,3,3',4'-tetramethyldiphenylmethane and 2,2',3,3'-tetramethyldiphenylmethane to isomerization reaction in the presence of a catalyst to convert into 3,3',4,4'-tetramethyldiphenylmethane. According to the process of the present invention, the objective 3,3',4,4'-tetramethyldiphenylmethane is efficiently obtained from tetramethyldiphenylmethane obtainable in particular by the reaction of o-xylene with formaldehyde. The 3,3',4,4'-tetramethyldiphenylmethane thus obtained can be converted by oxidation into 3,4,3',4'-benzophenonetetracarboxylic acid dianhydride which is important as a raw material for heat-resistant high molecular compounds.

11 Claims, No Drawings

PROCESS FOR PRODUCING 3,3',4,4'-TETRAMETHYLDIPHENYLMETHANE

BACKGROUND OF THE INVENTION

1. Field of the Invention

The present invention relates to a process for producing 3,3',4,4'-tetramethyldiphenylmethane. More particularly, it pertains to a process for efficiently producing 3,3',4,4'-tetramethyldiphenylmethane, the intermediary raw material for 3,4,3',4'-benzophenonetetracarboxylic dianhydride which is important as the starting material for the carboxylic acid component that is the raw material for polyimide resin and as that for heat resistant high molecular compounds such as the curing agent for epoxy resins.

2. Description of the Related Arts

It has heretofore been known that 3,3',4,4'-tetramethyldiphenylmethane (hereinafter sometimes referred to as "3,3',4,4'-TMDM") is useful as the starting material to be oxidized into 3,4,3',4'-benzophenonetetracarboxylic dianhydride (hereinafter sometimes referred to as "BTDA"), but nothing has been known regarding the process for efficiently producing 3,3',4,4'-TMDM in high yield. Thus, BTDA has been produced by the process wherein two molecules of o-xylene and one molecule of acetaldehyde are subjected to condensation reaction in the presence of a large amount of sulfuric-acid catalyst to provide 1,1-bis(3,4-dimethylphenyl)ethane, which is then oxidized by nitric acid to anhydrate itself into BTDA as the product.

The above-mentioned conventional process, however, has suffered the disadvantage that relatively large amounts of isomers and high boiling substance are produced as the by-products, which are not only unusable but also responsible for decrease in the yield of the objective product in the oxidation step.

Aside from the above, o-xylene and formaldehyde are reacted in the presence of such acid catalyst as sulfuric acid or p-toluenesulfonic acid to produce tetramethyldiphenylmethane (hereinafter sometimes referred to as "TMDM"), which however, contains three types of major isomers, namely 3,3',4,4'-TMDM; 2,3,3',4'-tetramethyldiphenylmethane (hereinafter sometimes referred to as "2,3,3',4'-TMDM"); and 2,2',3,3'-tetramethyldiphenylmethane (hereinafter sometimes referred to as "2,2'3,3'-TMDM").

Having a higher melting point as compared with the other isomers, the objective 3,3',4,4'-TMDM can be separated and recovered from TMDM containing the above-mentioned three types of isomers by means of crystallization (refer to Vopr. Khim. Tekhnol., 71,112–114 (1983), USSR).

However, the aforestated conventional process alone wherein the catalyst such as sulfuric acid or p-toluenesulfonic acid is employed to produce TMDM, from which 3,3',4,4'-TMDM is separated and recovered by means of crystallization is available only in low yield of the objective 3,3',4,4'-TMDM. It is, therefore, necessary to contrive the improvement in the yield of the objective 3,3',4,4'-TMDM by improving the selectivity of reaction and the like.

SUMMARY OF THE INVENTION

An intensive research and investigation made by the present inventors on the improvement in the yield of 3,3',4,4'-TMDM produced from TMDM led to the finding that a TMDM with a relatively low content of 3,3',4,4'-TMDM is isomerized into a TMDM with a high content of 3,3',4,4'-TMDM by the use of a catalyst. The present invention has been accomplished on the basis of the foregoing finding and information.

It is a general object of the present invention to provide a novel process for producing 3,3',4,4'-TMDM in high yield from TMDM containing different isomers which is obtained by the condensation reaction of o-xylene and formaldehyde.

It is another object of the present invention to improve the yield of 3,3',4,4'-TMDM from TMDM obtained by the condensation reaction of o-xylene with formaldehyde.

It is still another object of the present invention to efficiently produce BTDA from o-xylene and formaldehyde as the starting materials.

Thus the present invention provides a process for producing 3,3',4,4'-TMDM which comprises subjecting TMDM containing at least one of 2,3,3',4'-TMDM and 2,2',3,3'-TMDM to isomerization reaction in the presence of a catalyst into In addition, the present invention provides a process for producing BTDA which comprises the steps of subjecting TMDM as the starting material obtained by the reaction of o-xylene with formaldehyde in the presence of a catalyst to isomerization reaction into 3,3',4,4'-TMDM in the presence of a catalyst, recovering 3,3',4,4'-TMDM thus produced by separating from the resultant reaction products while reusing the residual liquid other than said 3,3',4,4'-TMDM by mixing the liquid in the above-mentioned starting material and oxidizing 3,3',4,4'-TMDM thus recovered in the presence or absence of a catalyst.

DESCRIPTION OF THE PREFERRED EMBODIMENT

Any TMDM containing 2,3,3',4'-TMDM and/or 2,2',3,3'-TMDM may be employed as the starting material for isomerization reaction in the present invention without specific limitation to the process for producing itself. In general, the TMDM can be produced by the known process in which o-xylene and formaldehyde are subjected to condensation reaction in the presence of the conventional acid catalyst such as sulfuric acid or p-toluenesulfonic acid, which process is disclosed in the specification of U.S. Pat. No. 2,848,509, etc.

In order to prevent the formation of high boiling substances in the isomerization reaction according to the present invention, a solvent such as an aromatic hydrocarbon may be used, of which o-xylene is most desirably used as the reaction solvent for the purpose of enhancing the selectivity of the reaction.

As the isomerization catalyst to be used in the present invention, the conventional catalyst for alkylation and/or isomerization reaction may be used. Although not necessarily clear in the reaction mechanism, the isomerization reaction is presumed to take place simultaneously as an intermolecular transalkylation reaction in addition to the intramolecular isomerization reaction with the result that a large proportion of 3,3',4,4'-TMDM is produced.

The specific examples of the catalyst for isomerization reaction to be used in the present invention include Bronsted acid such as hydrofluoric acid, sulfuric acid and phosphoric acid, Fridel-Craft catalyst such as HCl-AlCl$_3$ and HF-BF$_3$, Lewis acid such as aluminum chloride, antimony pentachloride, ferric chloride, tin chloride, titanium chloride and boron trifluoride and zeolite catalyst, among which HCl—AlCl₃, HF—BF₃, AlCl₃ and zeolite catalyst are preferably used.

Particularly desirable among various types of zeolite catalyst is the crystalline aluminosilicate zeolite, which is the cation-substituted type activated zeolite belonging to twelve-membered oxygen ring structure zeolite typified by Y-type zeolite.

The typical substituted cation includes hydrogen, ammonia, metallic cation and mixture thereof. Of the substituted metallic cations, rare earth element cations and alkaline earth metal cations are particularly desirable.

In the case where the catalyst of HCl—AlCl₃, HF—BF₃ or AlCl₃ is used in the isomerization reaction, the reaction may be carried out by either of a batchwise system and a continuous flow system, whereas in the case of a zeolite being used, a continuous flow system is preferable.

The isomerization reaction can be effected under a variety of conditions, and the suitable condition may be selected according to each situation. The preferable condition of isomerization reaction, however, consists in reaction temperatures ranging from $-15°$ C. to 300° C. and the reaction pressures in the range of 0.1 to 30 atom. A reaction temperature higher than 300° C. tends to accelerate side reactions which form high boiling substances, sometimes accompanied by the rearrangement of the methyl groups in an aromatic ring.

When TMDM is produced by the conventional process, that is, the known process in which o-xylene and formaldehyde are subjected to condensation reaction in the presence of a catalyst at a relatively low selectivity of 3,3',4,4'-TMDM, followed by the performance of the above-described isomerization reaction by the use of the resultant TMDM as the starting material, the selectivity of 3,3',4,4'-TMDM can be enhanced. Moreover, when the resultant 3,3',4,4'-TMDM is separated from the reaction products after the isomerization reaction while the residual liquid after the separation is recycled and mixed in the starting material to be isomerized and the isomerization reaction is repeated, the yield of the resultant 3,3',4,4'-TMDM is improved.

The oxidation of the 3,3',4,4'-TMDM thus obtained in the presence or absence of a catalyst affords BTDA. The oxidation may be effected by means of a known air oxidation or nitric acid oxidation and specifically exemplified by (1) air oxidation process wherein air is blown into acetic acid solvent containing 3,3',4,4'-TMDM at a high temperature and a high pressure in the presence of a catalyst of heavy metal series and (2) nitric acid oxidation process wherein oxidation is carried out in the presence of 20 to 40% by weight of aqueous solution of nitric acid at a high temperature and a high pressure.

The oxidation of the 3,3',4,4'-TMDM usually results in the formation of 3,3',4,4'-benzophenonetetracarboxylic acid (hereinafter sometimes referred to as "BTDA"), which is anhydrated by the known process to afford the objective BTDA.

As described hereinbefore, the process according to the present invention enables the improvement in the yield of 3,3',4,4'-TMDM produced from TMDM with a low 3,3',4,4'-TMDM content as well as the efficient production of more useful BTDA from the resultant 3,3'4,4'-TMDM.

The present invention will be described in more detail with reference to the following non-limitative examples, in which the substances in the oil phase were analyzed by means of gas chromatography. Example 1

In a 500 ml autoclave were placed 36 g of TMDM as the starting material for isomerization reaction having an isomer composition of 36.9% of 3,3',4,4'-TMDM; 57.4% of 2,3,3',4'-TMDM; and 5.7% of 2,2',3,3'-TMDM, 34 g of o-xylene as the solvent and 58 g of hydrofluoric acid and 3.3 g of boron trifluoride each as the catalyst to effect isomerization reaction with stirring at $-4°$ C. and 0.8 kg/cm²G for one hour.

After the reaction was completed, the reaction liquid was neutralized and washed with water, and the oil phase was recovered in an amount of 68.7 g with the analytical value of 54.5% by weight of o-xylene and 35.4% by weight of TMDM.

The resultant TMDM had an isomer composition of 92.0% of 3,3',4,4'-TMDM and 8.0% of 2,3,3',4'-TMDM.

EXAMPLE 2

In a 200 ml three-neck flask equipped with a stirring rod, a thermometer and a cooler were placed 11.2 g of TMDM as the starting material for isomerization reaction having an isomer composition of 36.9% of 3,3',4,4'-TMDM; 57.4% of 2,3,3',4'-TMDM; and 5.7% of 2,2',3,3'-TMDM, 10.6 g of o-xylene as the solvent and 2.66 g of aluminum chloride anhydride as the catalyst with cooling to 0° C.

After isomerization reaction at 0° C. for 2 hours, the aluminum chloride was decomposed with water to remove itself, and the oil phase was washed with water three times and dehydrated with sodium sulfate anhydride to afford 20.8 g of the product as the oil phase.

The above-mentioned reaction liquid had a composition containing 50.8% by weight of o-xylene, 44.2% by weight of TMDM and 5.0% by weight of miscellaneous products other than the above two.

The resultant TMDM had an isomer composition of 91.8% of 3,3',4,4'-TMDM and 8.2% of 2,3,3',4'-TMDM.

EXAMPLE 3

Preparation of catalyst

The zeolite catalyst of HY, CeY and CaY type each as used in the present example were synthesized according to Example 2 in the specification of Japanese Patent Publication No. 1639/1961.

The ion exchange procedure was carried out at 90° C. for 16 hours by separately using 0.5N aqueous solution of ammonia hydrochloride, 0.5N aqueous solution of cerium chloride and 0.5N aqueous solution of calcium chloride each, followed by washing with water twice and drying at 150° C. for 2 hours.

The preliminarily dried catalyst in powder form was compression molded to form tablet, which was milled in a mortar, classified with a screen and adjusted to 10 to 42 mesh. The ammonium-substituted Y-type zeolite was calcined at 560° C. for 3 hours in a stream of nitrogen to be converted to H-type zeolite.

Isomerization reaction

With o-xylene was mixed TMDM having an isomer composition of 42.6% of 3,3',4,4'-TMDM; 53.8% of 2,3,3',4'-TMDM; and 3.6% of 2,2',3,3'-TMDM to produce o-xylene solution containing 51.4% by weight of TMDM as the starting material to be isomerized.

In a 12 ml closed-type reactor made of stainless steel were placed 6 g of the above-mentioned starting material and 2 g of the afore-said catalyst which had been dried at 300° C. for 2 hours immediately before use. Then the reactor was put in an oil bath which had been adjusted to a prescribed temperature and equipped with a shaker to carry out isomerization reaction under stirring for a predetermined time. Immediately after the reaction was completed, the reactor was taken out of the oil bath and cooled with water. Then the reaction liquid was taken out of the reactor and analyzed for composition thereof. The result is given in Table 1 for each of the above-described catalysts.

TABLE 1

(Starting material and catalyst used, and composition of the resultant reaction liquid)

| Type of catalyst, etc. | Starting material | HY | HY | CeY | CeY | CeY | CaY |
|---|---|---|---|---|---|---|---|
| Reaction temperature (°C.) | — | 110 | 120 | 120 | 160 | 180 | 200 |
| Reaction time (hr) | — | 3 | 3 | 3 | 3 | 2 | 3 |
| Compositon of reaction liquid (wt %) | | | | | | | |
| o-xylene | 48.6 | 48.1 | 49.7 | 48.1 | 49.9 | 52.0 | 49.8 |
| TMDM | 51.4 | 43.7 | 39.9 | 43.5 | 31.2 | 23.4 | 36.4 |
| Other products | 0 | 8.2 | 10.4 | 8.4 | 18.9 | 24.6 | 13.8 |
| Composition of TMDM isomer (%) | | | | | | | |
| 3,3',4,4'-TMDM | 42.6 | 79.5 | 84.6 | 77.9 | 79.4 | 81.2 | 76.6 |
| 2,3,3',4'-TMDM | 53.8 | 19.5 | 15.4 | 21.0 | 20.6 | 18.8 | 22.4 |
| 2,2',3,3'-TMDM | 3.6 | 1.0 | 0 | 1.1 | 0 | 0 | 1.0 |

EXAMPLE 4

A 30 ml catalyst-packed type continuous reactor made of stainless steel was packed was 8.0 g of the catalyst HY as prepared in the preceding Example 3, which then was dried at 300° C. for 3 hours in a stream of nitrogen.

Thereafter the starting material as prepared in Example 3 was continuously fed to the reactor to proceed with isomerization reaction at a reaction temperature of 120° C. under ordinary pressure at a weight hourly space velocity of 0.926 hr$^{-1}$.

The composition of the reaction liquid after 24 hours of reaction indicated 52.0% by weight of o-xylene, 39.3% by weight of TMD and 8.7% by weight of miscellaneous products other than the above two. The resultant TMDM had an isomer composition of 76.6% of 3,3',4,4'-TMDM, 21.7% of 2,3,3',4'-TMDM and 1.7% of 2,2',3,3'-TMDM.

EXAMPLE 5

Synthesis of TMDM

In a two liter flask equipped with a stirring rod, a thermometer and a cooler were placed 425 g (4 mol) of o-xylene and 306 g (2 mol) of 64% sulfuric acid. Then, 81 g (1 mol) of 37% aqueous solution of formaldehyde was added dropwise to the above mixture in the flask at 121° C. under reflux for 3 hours. After the completion of the addition, the mixture was stirred for one hour. The product after reaction was allowed to stand for 30 minutes for cooling and liquid separation. The oil phase thus separated was washed with water 3 times and dehydrated with sodium sulfate anhydride to afford 427 g of the reaction liquid as the oil phase (R-1).

A sample taken from the reaction liquid thus obtained was analyzed for the composition. The result was 52.5% by weight of o-xylene, 38.1% by weight of TMDM and 9.4% by weight of miscellaneous products other than the above two. The resultant TMDM had an isomer composition of 59.4% of 3,3',4,4'-TMDM, 37.4% of 2,3,3',4'-TMDM and 3.2% of 2,2',3,3'-TMDM.

The yield based on formaldehyde (hereinafter referred to as "Yield") was 72.6 mol % of TMDM and 43.1 mol % of 3,3',4,4'-TMDM.

Distillation

Of 427 g of the oil phase (R-1) after dehydration, 217 g thereof was sampled and distilled under reduced pressure. As the result, 109 g of o-xylene was recovered and 77 g of TMDM was obtained as the distillate at a boiling point of 162° C. under a pressure of 4 mmHg.

The 24 g of bottom residue (R-2) after TMDM distillation contained 16.0% by weight of TMDM having an isomer composition of 65.8% of 3,3',4,4'-TMDM and 34.2% of 2,3,3',4'-TMDM.

Separation of 3,3',4,4'-TMDM 77 g of TMDM as separated by distillation was cooled to 1° C. to crystallize 3,3',4,4'-TMDM, which was separated by filtration to afford 39 g of crude 3,3',4,4'-TMDM having a purity of 80.5% by weight. The filtrate after filtration is referred to as F-1.

The crude 3,3',4,4'-TMDM was recrystallized from 80 g of ethanol at 5° C. and the crystal thus obtained was separated by filtration. The filtrate after the filtration is referred to as F-2.

The aforementioned crystal was melted at 60° C., and ethanol therein was distilled away to provide 27 g of 3,3',4,4'-TMDM as the product having a purity of 99.3% by weight and a melting point of 39° C.

The ethanol was distilled away from the filtrate (F-2) of the recrystallization and the residue was mixed with the filtrate (F-1) of the crystallization to form mother liquor after the separation of 3,3',4,4'-TMDM. The mother liquor had an isomer composition of 37.2% of 3,3',4,4'-TMDM, 57.6% of 2,3,3',4'-TMDM and 5.2% of 2,2',3,3'-TMDM.

Isomerization reaction

In a 1000 ml three-neck flask equipped with a stirring rod, a thermometer and a cooler were introduced, as a starting material for isomerization, a mixture of 210 g of R-1 (oil phase of the reaction liquid) which was not distilled (total R-1 of 427 g minus distilled amount of 217 g), 24 g of the bottom residue (R-2), 48 g of R-3 (the mother liquor after the separation of 3,3',4,4'-TMDM) and 109 g of o-xylene recovered by distillation (material composition by weight: 56.0% of o-xylene, 33.8% of TMDM and 10.2% of others and isomer composition of TMDM: 51.4% of 3,3',4,4'-TMDM, 44.7% of 2,3,3',4'-TMDM and 3.9% of 2,2',3,3'-TMDM) and 47.7 g of aluminum chloride anhydride as the catalyst to effect reaction at 18° C. for 2 hours.

After the end of the reaction, the aluminum chloride was decomposed with water to remove itself, and the oil phase was washed with water three times and dehydrated with sodium sulfate anhydride to afford 387 g of the product as the oil phase.

The aforementioned reaction liquid had a composition by weight of 54.2% of o-xylene, 43.7% of TMDM and 2.1% of other products than the above two.

The above-mentioned TMDM had an isomer composition of 91.5% of 3,3',4,4'-TMDM and 8.5% of 2,3,3',4'-TMDM.

The overall yield of the 3,3',4,4'-TMDM was 81.1 mol % including the 3,3',4,4'-TMDM with 99.3% purity by weight which was recovered in the 3,3',4,4'-TMDM separation step of the present Example.

EXAMPLE 6

In a one liter antoclave equipped with a stirrer, a thermometer and an external heater were placed 37.5 g (0.165 mol) of the synthesized 3,3',4,4'-TMDM and 458.4 g (2.13 mol as $HNO_3$) of 30% $HNO_3$. The mixture was pressurized with nitrogen gas to 1 kg/cm$^2$G and heated up to 210° C. at a temperature-rise rate of 70° C./hour under stirring initiated simultaneously with the initiation of the temperature raising. After the temperature reached 210° C., the heating with stirring was continued for 3 hours followed by cooling of the autoclave to room temperature to conclude the reaction. The gas inside the autoclave was released, and to a flask was transferred the content therein, which was yellowish green liquid containing crystals. Then, the liquid was evaporated to bone dryness with an oil bath at 120° to 140° C. to afford crude BTA in the form of yellowish white powder having an acid value of 612.9 mg KOH/g at a Yield of 150.3% by weight.

To 35 g of crude BTA thus obtained were added 350 g of acetic anhydride as the solvent and 1.75 g of granular activated carbon. The mixture was heated at 100° C. with stirring for one hour, followed by filtration for removing the insolubles including the used activated carbon. The solvent was removed from the filtrate at a reduced pressure of 60 mmHg to crystallize and separate purified BTDA as the product.

The purified BTDA as obtained at a crystallization rate of 65.4% had an acid value of 691.0 mgKOH/g, a melting point of 223° C. and a Gardner color scale of No. 6 for the melt.

What is claimed is:

1. A process for producing 3,3',4,4'-tetramethyldiphenylmethane which comprises isomerizing a tetramethyldiphenylmethane containing at least one of 2,3,3',4'-tetramethyldiphenylmethane and 2,2',3,3'-tetramethyldiphenylmethane in the presence of a catalyst and a solvent to convert said tetramethyldiphenylmethane into 3,3',4,4'-tetramethyldiphenylmethane, wherein the catalyst is at least one catalyst selected from the group consisting of a Bronstead acid, a Lewis acid, a Friedel-Crafts catalyst and a zeolite catalyst and the solvent is o-xylene.

2. The process according to claim 1, wherein the tetramethyldiphenylmethane is produced by the reaction of o-xylene with formaldehyde.

3. The process according to claim 1, wherein the catalyst comprises at least one compound selected from the group consisting of hydrofluoric acid, hydrochloric acid, sulfuric acid, phosphoric acid, aluminum chloride, antimony pentachloride, ferric chloride, tin chloride, titanium chloride and boron trifluoride.

4. The process according to claim 1, wherein the catalyst is HCl-AlCl$_3$ or HF-BF$_3$.

5. The process according to claim 1, wherein the catalyst is a crystalline aluminosilicate zeolite catalyst.

6. The process according to claim 1, wherein the isomerizing is effected at a temperature of $-15°$ C. to 300° C. under a pressure of 0.1 to 30 atm.

7. The process according to claim 3, wherein the isomerizing is carried out at a temperature of $-15°$ C. to 300° C. and at a pressure of 0.1 to 30 atm.

8. The process according to claim 4, wherein the isomerizing is carried out at a temperature of $-15°$ C. to 300° C. and at a pressure of 0.1 to 30 atm.

9. The process according to claim 5, wherein the isomerizing is carried out at a temperature of $-15°$ C. to 300° C. and at a pressure of 0.1 to 30 atm.

10. The process according to claim 5, wherein the zeolite catalyst is a Y-type zeolite.

11. The process according to claim 10, wherein the isomerizing is carried out at a temperature of $-15°$ C. to 300° C. and at a pressure of 0.1 to 30 atm.

* * * * *